United States Patent [19]

Ueda et al.

[11] Patent Number: 4,919,925

[45] Date of Patent: Apr. 24, 1990

[54] DEODORANT, DEODORIZING COMPOSITE MATERIAL, DEODORIZING RESIN COMPOSITION, DEODORIZING RESIN ARTICLES AND DEODORIZING FOAM

[75] Inventors: Tsunehisa Ueda; Kouji Miyazaki, both of Kawasaki; Tadao Natsuume, Yokosuka, all of Japan

[73] Assignee: Nippon Zeon Co., Ltd., Tokyo, Japan

[21] Appl. No.: 218,551

[22] Filed: Jul. 13, 1988

[30] Foreign Application Priority Data

Jul. 17, 1987 [JP] Japan .................................. 62-178663
Sep. 11, 1987 [JP] Japan .................................. 62-228052

[51] Int. Cl.$^5$ .................................................. A61L 2/16
[52] U.S. Cl. ........................................ 424/76.1; 422/5; 424/76.5; 424/76.6; 424/76.7; 424/76.21
[58] Field of Search ................... 424/76.1, 76.21, 76.5, 424/76.6, 76.7; 422/5; 549/236, 240, 255

[56] References Cited

U.S. PATENT DOCUMENTS

| | | | |
|---|---|---|---|
| 3,412,111 | 11/1968 | Irwin et al. | 549/255 |
| 3,873,643 | 3/1975 | Wu et al. | 525/193 |
| 3,976,590 | 8/1976 | Yax et al. | 252/182 |
| 3,985,504 | 10/1976 | Kindscher et al. | 422/13 |
| 4,003,959 | 1/1977 | Wada et al. | 525/137 |
| 4,127,497 | 11/1978 | Rierson | 252/182 |
| 4,339,550 | 7/1982 | Palinczar et al. | 424/76.3 |
| 4,342,665 | 8/1982 | Itoh et al. | 252/316 |
| 4,376,789 | 5/1983 | Lowicki et al. | 424/361 |
| 4,522,978 | 6/1985 | Gardner | 525/48 |
| 4,532,297 | 7/1985 | Gardner | 525/48 |
| 4,731,418 | 3/1988 | Dean | 525/205 |

FOREIGN PATENT DOCUMENTS

| | | | |
|---|---|---|---|
| 0160738 | 12/1979 | Japan | 424/76.7 |
| 0036057 | 2/1985 | Japan | 424/76.6 |
| 2112554 | 5/1987 | Japan | 424/76.1 |
| 2129183 | 6/1987 | Japan | 424/76.1 |
| 2179464 | 8/1987 | Japan | 424/76.1 |

Primary Examiner—Ellis P. Robinson
Assistant Examiner—Archene A. Turner
Attorney, Agent, or Firm—Sherman and Shalloway

[57] ABSTRACT

A deodorant comprising a Diels-Alder reaction-type adduct of an alpha,beta-unsaturated dicarboxylic acid anhydride and an olefin or a derivative of the adduct as an active ingredient. A composite material, a resin composition, a resin article and a foam each containing the deodorant.

4 Claims, No Drawings

DEODORANT, DEODORIZING COMPOSITE MATERIAL, DEODORIZING RESIN COMPOSITION, DEODORIZING RESIN ARTICLES AND DEODORIZING FOAM

This invention relates to a deodorant, a deodorizing composite material, a deodorizing resin composition and a deodorizing resin article. More specifically, it relates to a deodorant having excellent deodorizing ability and a deodorizing composite material, a deodorizing resin composition, a deodorizing resin article and a deodorizing foam each containing the deodorant.

It has been known that aliphatic polycarboxylic acids such as citric acid and oxalic acid and their salts are effective as agents for removing basic malodors such as ammonia and amine smells (see, for example, Japanese Laid Open Patent Publications Nos. 137565/1986 and 154673/1986). It was reported that deodorizing resin compositions are obtained by incorporating these compounds in thermoplastic resins (Japanese Laid-Open Patent Publication No. 209662/1986). These compounds and resin compositions, however, do not sufficiently have the ability to deodorize other malodorous components.

The present inventors have now found, as a result of extensive investigations made in order to solve the above problem of the prior art, that a deodorant having an excellent deodorizing action not only on basic malodorous components but also on hydrogen sulfide can be obtained by using a Diels-Alder reaction-type adduct of an alpha,beta-unsaturated dicarboxylic acid anhydride and an olefin or a derivative of the adduct, and that a resin composition having an excellent deodorizing action can be obtained by incorporating the deodorant in a thermoplastic resin.

The present invention provides a deodorant comprising a Diels-Alder reaction-type adduct of an alpha,beta-unsaturated dicarboxylic acid anhydride and an olefin or a derivative of the adduct as an active ingredient; a deodorizing composite material obtained by including the deodorant in a substrate; a deodorizing resin composition obtained by incorporating the deodorant in a thermoplastic resin; and a deodorizing shaped article and a deodorizing foam obtained by processing the resin composition.

The Diels-Alder reaction-type adduct used in this invention may be, for example, a product obtained by the Diels-Alder reaction of an alpha,beta-unsaturated dicarboxylic acid anhydride with a diolefin and a product of the ene reaction of an alpha,beta-unsaturated with an olefin [the ene reaction is described in H. M. R. Hoffmann, Angew. Chem. Int. Ed. 8, 556 (1969)].

Specific examples of the alpha,beta-unsaturated dicarboxylic acid anhydride used in the Diels-Alder reaction-type addition reaction are maleic anhydride, itaconic anhydride and citraconic anhydride. Maleic anhydride is preferred because of its reactivity and economy.

The diolefin to be used in the Diels-Alder reaction with the alpha,beta-unsaturated dicarboxylic acid anhydride is not particularly limited. Its specific examples include aliphatic conjugated diolefins such as butadiene, isoprene and piperylene; aliphatic trienes such as 1,3,5-hexatriene; cyclic conjugated polyunsaturated olefins such as cyclopentadiene, 1,3-cyclohexadiene and cyclooctatetraene; and aromatic compounds such as styrene, indene and naphthalene. The diolefins described in M. C. Kloetzel et al., "Organic Reactions", vol. 4, pages 1–60 (John Wiley & Sons, Inc.) may also be cited as other examples of the diolefin.

The olefin to be used in the ene reaction with the alpha,beta-unsaturated dicarboxylic acid anhydride is not particularly limited. As its specific examples, there may be cited aliphatic monolefins such as propylene, isobutene, 1-butene, 2-butene, 1-pentene, 2-pentene, 2-methyl-1-butene, 2-methyl-2-butene, 1-hexene, 2,2,4-trimethyl-1-pentene, 2,2,4-trimethyl-2-pentene, 1-decene, 1-octadecene, and alpha-olefins obtained by polymerizing lower monolefins (e.g., ethylene or propylene) with Ziegler catalysts; cyclic monolefins such as cyclopentene, cyclohexene and cyclooctene; aliphatic or cyclic non-conjugated diolefins such as 1,4-pentadiene and 1,4-cyclohexadiene; higher unsaturated fatty acids such as oleic acid; and polymers having an unsaturated bond such as polybutadiene.

One or more of the hydrogen atoms of these compounds may be substituted, for example by an alkyl group or a phenyl group.

The derivative of the aforesaid Diels-Alder reaction-type adduct used in this invention is not restricted in the method of synthesis. It may be of any structure derived from the Diels-Alder reaction-type adduct by known reactions. One specific example is a hydrogenation product of the adduct.

The deodorant of this invention may comprise at least one Diels-Alder reaction-type adduct of the alpha,beta-unsaturated dicarboxylic acid and olefins or at least one derivative thereof.

Conventional deodorants, fungicides and mold-proofing agents and various additives such as pigments, coloring agents, stabilizers and antioxidants may, as required, be incorporated in the deodorant of this invention if they do not impair the effect of the deodorant of this invention.

The deodorant of the invention may be used alone in the form of, for example, a solution, a powder or a tablet, or be incorporated in various substrates to form deodorizing composite materials.

The substrates used in the composite materials of this invention are not particularly limited if they permit inclusion of the deodorant of the invention by impregnation, coating, deposition or otherwise. Specific examples are paper, cloths, foamed sheets, pulp, fibers, activated carbon, alumina, silica gel, zeolite, clay, bentonite, diatomaceous earth and acid clay. The substrates may be in the form of, for example, a powder, granules, fibers or a sheet.

The amount of the deodorizing agent to be included in the substrate in the deodorizing composite material of this invention differs with the purpose for which the composite material is used and is usually 0.1 to 30% by weight, preferably 1 to 20% by weight, based on the substrate. If its amount is excessively small, the function of the deodorant might be insufficient. Excessively large amounts, on the other hand, will be economically disadvantageous.

By incorporating the deodorant of the invention in a thermoplastic resin, a deodorizing resin composition can be obtained. This composition is useful as a material for deodorizing resin articles.

The thermoplastic resin used in this invention may be any thermoplastic resin which can be shaped into films, sheets, fibers, foams, and various other articles. Specific examples include polyolefins such as polyethylene, polypropylene and polybutadiene; vinyl polymers such as polyvinyl alcohol, polyvinyl chloride, polyvinylidene chloride, polystyrene, acrylonitrile/butadiene/styrene copolymer, vinyl chloride/vinyl acetate copolymer and ethylene/vinyl acetate copolymer; block copolymers between aromatic vinyl compounds and conjugated diene monomers such as styrene/isoprene block copolymer and styrene/butadiene block copolymer; cellulose esters such as cellulose diacetate; regenerated cellulose; polyesters; polyamides; and fluorocarbon resins. Examples of foamable thermoplastic resins are polyvinyl chloride, vinyl acetate/vinyl chloride copolymer, polyethylene, polypropylene, polystyrene, acrylonitrile/butadiene/styrene resin, polyvinyl alcohol, polyamides and cellulose.

The amount of the deodorant of this invention to be incorporated in the thermoplastic resin varies with the purpose for which the deodorizing resin composition is used, and is usually 0.1 to 30% by weight, preferably 10 to 20% by weight. If its amount is excessively small, the deodorizing function of the resulting resin will become insufficient.

The method of incorporating the deodorant in the thermoplastic resin is not particularly limited. For example, all the deodorant may be added to the thermoplastic resin at a time, or it is possible to add part of the deodorant to the thermoplastic resin, and add the remainder later. It is also possible to add the deodorant to part of the thermoplastic resin and add the remainder of the thermoplastic resin to the resulting mixture. A product obtained by supporting the deodorant of the invention on an inorganic support such as activated carbon is suitable for incorporation because it has good dispersibility in the thermoplastic resin.

The deodorizing resin composition of this invention may, as required, contain conventional deodorants, fungicides and mold-proofing agents and various additives such as stabilizers, lubricants, antioxidants, ultraviolet absorbers, processing coagents, blowing agents, pigments, fire retardants, and impact resisting coagents.

The deodorizing resin composition of this invention so obtained can be shaped into various articles such as films and sheets by ordinary resin shaping methods such as extrusion, compression molding, calender molding, blow molding, injection molding, thermoforming, lamination and rotational molding.

The deodorizing resin composition of this invention, alone or together with another fiber-forming material, may be spun into fibers. Fine holes may be formed on the resulting films or sheets by, for example, needle punching in order to impart air permeability. It is also possible to cover them with cloths, nonwoven cloths or paper, or laminate them on films prepared from other resins. The fibers may be woven into cloths or nets.

When the thermosetting resin is foamable, the resulting deodorizing resin composition may be foamed and molded to produce a deodorizing foamed article.

The method of forming the deodorizing foam of this invention is not particularly limited. For example, all the deodorant is premixed with the foamable thermoplastic resin, and then the mixture is foamed and molded by a conventional method. It is also possible to mix part of the deodorant with the foamable thermoplastic resin and foam and mold the mixture, and then include the remainder of the deodorant in the foamed article by impregnation.

The production of a foamed article from the deodorizing resin composition of the invention has the advantage that malodors from ammonia, etc. occurring during foaming of the resin can be drastically reduced, and the resulting foamed article has a high expansion ratio.

The invention can give a deodorant having better deodorizing ability than those obtained in the prior art. The deodorant can be used alone or as a deodorizing composite material by including it in a substrate. Furthermore, by incorporating the deodorant of the invention in a thermoplastic resin, a deodorizing resin composition having excellent deodorizing ability can be obtained. The deodorizing resin composition is useful as a material for the production of films, sheets, fibers, foams and other various plastic articles having deodorizing or odor eliminating functions. The resulting articles are useful as materials for producing various articles such as apparel, beddings, furniture, wallpaper, food receptacles, packaging materials and filters.

The following examples illustrate the present invention more specifically. All parts and percentages in the following Examples, Comparative Examples and Referential Examples are by weight unless otherwise specified.

REFERENTIAL EXAMPLE 1

In each run, each of the alpha-olefins shown in Table 1 and an equimolar amount of maleic anhydride were fed into an autoclave and reacted at 200° C. for 15 hours in the presence of a polymerization inhibitor. The unreacted alpha-olefin was removed under reduced pressure. As a result, ene reaction products (to be sometimes referred to an "ene-adduct") I to VI between the alpha-olefins and the alpha,beta-unsaturated dicarboxylic acid anhydride as a component of a deodorant were obtained.

TABLE 1

| Ene-adduct | I | II | III | IV | V | VI |
|---|---|---|---|---|---|---|
| alpha-Olefin and its carbon number | A*1 6-10 | B*2 12-14 | C*3 16-18 | D*4 20-28 | E*5 30-40 | F*6 12 |
| Properties of the adduct | | | | | | |
| Melting point (°C.) | −37 | 26 | 43 | 52 | 50 | 13 |
| Saponification value (KOH mg/g) | 537 | 361 | 312 | 222 | 192 | 421 |

*1 DIALEN 610 (a product of Mitsubishi Chemical Industries, Ltd.)
*2 DIALEN 124 (a product of Mitsubishi Chemical Industries, Ltd.)
*3 DIALEN 168 (a product of Mitsubishi Chemical Industries, Ltd.)
*4 DIALEN 208 (a product of Mitsubishi Chemical Industries, Ltd.)
*5 DIALEN 30 (a product of Mitsubishi Chemical Industries, Ltd.)
*6 56N Polymer F-2 (a product of Nippon Petrochemical Co., Ltd.)

REFERENTIAL EXAMPLE 2

Maleic anhydride (68.6 parts) and 70 parts of toluene were fed into an autoclave, and melted at 55° C. Then, 0.162 part of hydroquinone was added. Subsequently, 30.9 parts (corresponding to 1.1 moles of trans-1,3-pentadiene per mole of maleic anhydride) of crude trans-1,3-pentadiene composed of 40% of trans-1,3-pentadiene, 20% of cis-1,3-pentadiene and 40% of pentanes was continuously added over 6 hours at 50° C. The temperature was then elevated to 60° C. and the reaction was carried out for 3 hours. After the reaction, the volatile components were removed by distillation at 90° C. under atmospheric pressure. As the Diels-Alder reaction product, 3-methyltetrahydrophthalic anhydride (melting point 61° C.) was obtained in a yield of 99%.

EXAMPLE 1

The deodorants indicated in Table 1, 3-methyltetrahydrophthalic anhydride obtained in Referential Example 2, citric acid and malic acid were used as samples and subjected to an ammonia deodorizing test and a trimethylamine deodorizing test. After 24 hours, all the samples completely deodorized ammonia and trimethylamine. The same samples were subjected to a hydrogen sulfide deodorizing test, and the results are shown in Table 2.

These deodorizing tests were carried out by the following methods.

Ammonia and trimethylamine deodorizing tests

One gram of each sample was put in a 150 ml glass ampoule having a crown cap, and the ampoule was sealed up. The inside of the ampoule was replaced by air containing 100,000 ppm of ammonia or 10,000 ppm of trimethylamine. After a predetermined period of time, the amount of ammonia or trimethylamine in the ampoule was measured by gas chromatography.

Hydrogen sulfide deodorizing test

One gram of each sample was put in a 3-liter bag with a silicone rubber stopper, and then 1 liter of air containing 100 ppm of hydrogen sulfide was introduced into the bag. After a predetermined period of time, the amount of hydrogen sulfide in the bag was measured by a Kitagawa-type gas detecting tube.

TABLE 2

| | Run No. | Deodorant | Hydrogen sulfide deodorizing rate (%) (24 hours later) |
|---|---|---|---|
| Invention | 1-1 | adduct of maleic anhydride and alpha-olefin (I) | 100 |
| | 1-2 | adduct of maleic anhydride and alpha-olefin (II) | 100 |
| | 1-3 | adduct of maleic anhydride and alpha-olefin (III) | 100 |
| | 1-4 | adduct of maleic anhydride and alpha-olefin (IV) | 100 |
| | 1-5 | adduct of maleic anhydride and alpha-olefin (V) | 100 |
| | 1-6 | adduct of maleic anhydride and alpha-olefin (VI) | 100 |
| | 1-7 | 3-methyltetrahydrophthalic anhydride | 100 |
| Comparison | 1-8 | citric acid | 5 |
| | 1-9 | malic acid | 7 |

The results obtained in Example 1 show that the deodorants of this invention have a superior ability to deodorize basic malodors and a hydrogen sulfide malodor.

EXAMPLE 2

In each run, 100 parts of each of the thermoplastic resins indicated in Table 3 was mixed with each of the deodorant components indicated in Table 3 by a Henschel mixer to give a deodorizing resin composition. The resulting resin composition was extruded into a sheet from a T-die using an extruder having a cylinder inside diameter of 65 mm and a screw compression ratio of 5.0. The sheet was biaxially stretched to give each of films (1) to (9). The films (1) to (7) were colorless and transparent and uniform. The films (8) and (9) were colorless and transparent but the deodorant components were not well dispersed, and the presence of raised parts was observed.

TABLE 3

| | | Deodorant component | | |
|---|---|---|---|---|
| | Film | Type | Amount (parts) | Thermoplastic resin |
| Invention | (1) | adduct (I) | 2.5 | low-density polyethylene (*1) |
| | (2) | adduct (III) | 2.5 | low-density polyethylene (*1) |
| | (3) | adduct (V) | 2.5 | low-density polyethylene (*1) |
| | (4) | adduct (V) | 5.0 | low-density polyethylene (*1) |
| | (5) | adduct (V) | 10.0 | low-density polyethylene (*1) |
| | (6) | adduct (V) | 5.0 | polypropylene (*2) |
| | (7) | 3-methyltetrahydrophthalic anhydride | 5.0 | low-density polyethylene (*1) |
| Comparison | (8) | citric acid | 2.5 | low-density polyethylene (*1) |
| | (9) | malic acid | 2.5 | low-density polyethylene (*1) |

(*1): SHOLEX 720 FS produced by Showa Denko Kabushiki Kaisha
(*2): SHOW-ALLOMER MX-201 produced by Showa Denko Kabushiki Kaisha

EXAMPLE 3

Samples (250 mm in length and 150 mm in width) were prepared from films (1) to (9) shown in Table 4, and subjected to the same ammonia deodorizing test and hydrogen sulfide deodorizing test as in Example 1 except that the concentration of ammonia was changed to 5,000 ppm and the concentration of hydrogen sulfide was changed to 50 ppm. The results are shown in Table 4.

The results show that films prepared from the deodorizing compositions of this invention have an excellent ability to deodorize basic components and hydrogen sulfide.

TABLE 4

| | | Ammonia deodorizing rate (%) | | | Hydrogen sulfide deodorizing rate (%) |
|---|---|---|---|---|---|
| Film | | 1 hour later | 5 hours later | 24 hours later | 24 hours later |
| Invention | (1) | 29.8 | 81.9 | 100 | 100 |
| | (2) | 17.3 | 47.6 | 91.8 | 95 |
| | (3) | 10.7 | 29.3 | 56.5 | 75 |
| | (4) | 17.1 | 49.8 | 100 | 100 |
| | (5) | 28.9 | 79.1 | 100 | 100 |
| | (6) | 16.8 | 48.8 | 100 | 100 |
| | (7) | 32.8 | 84.0 | 100 | 100 |
| Comparison | (8) | 10 | 21 | 54 | 9 |
| | (9) | 4.9 | 9.0 | 15.2 | 7 |

EXAMPLE 4

To 100 parts of vinyl chloride resin (NIPEON A-43 produced by Nippon Zeon Co., Ltd.) were added 3 parts of a stabilizer (MARK AC-173, a Ba-Zn type stabilizer for vinyl chloride resins which was produced by Asahi Denka Kogyo K. K.), 4 parts of dodecenylsuccinic anhydride and 60 parts of dioctyl phthalate as a plasticizer, and they were mixed for 10 minutes by a mixing and grinding machine to form a paste sol. The sol was coated on a glass plate by a bar coater, and treated at 190° C. for 2 minutes in an oven to give a polyvinyl chloride film (10) having a thickness of 450 micrometers. The resulting film (10) was colorless and transparent.

EXAMPLE 5

A film (11) having a thickness of 450 micrometers was prepared in the same way as in Example 4 except that the ene-adduct IV was used instead of dodecenylsuccinic anhydride. The film (11) was colorless and transparent.

COMPARATIVE EXAMPLE 1

A film (12) having a thickness of 450 micrometers was prepared in the same way as in Example 4 except that trimellitic acid was used instead of dodecenylsuccinic anhydride. The film (12) was colored brown and non-transparent.

COMPARATIVE EXAMPLE 2

A film (13) having a thickness of 450 micrometers was prepared in the same way as in Example 4 except that a mixture of ferrous sulfate, citric acid and sodium citrate (mixing ratio=80:15:5) was used instead of dodecenylsuccinic anhydride. The film (13) was colored brown and non-uniform with the inclusion of numerous bubbles.

EXAMPLE 6

Deodorizing tests

Films (10) to (12) were subjected to the same deodorizing tests as in Example 3. The film (13) was not tested because it had a base shape. The results are shown in Table 5.

Table 5 shows that the deodorizing resin articles of this invention have an excellent ability to deodorize basic hydrogen sulfide malodors.

TABLE 5

| Film | | Ammonia deodorizing rate (%) | | | Hydrogen sulfide deodorizing rate (%) |
|---|---|---|---|---|---|
| | | 1 hour later | 5 hours later | 24 hours later | 24 hours later |
| Invention | (10) | 74 | 92 | 100 | 100 |
| | (11) | 70 | 90 | 100 | 100 |
| Comparison | (12) | 50 | 72 | 100 | 23 |

EXAMPLE 7

95 Parts of high-density polyethylene (SHOLEX F5012M produced by Showa Denko K. K.) and 5 parts of the ene-adduct III were mixed. The mixture was extruded from an extruder equipped with nozzles for monofilaments at a cylinder end temperature of 220° C. to form undrawn filaments. The as-extruded filaments were passed through a cooling tank at 30° C. and then drawn in boiling water at 100° C. to obtain filaments (1) having a size of 300 denier.

EXAMPLE 8

Filaments (2) having a size of 300 denier were produced in the same way as in Example 7 except that the ene-adduct V was used instead of the ene-adduct III.

EXAMPLE 9

Filaments (3) having a size of 300 denier were produced in the same way as in Example 7 except that polypropylene (SHO-ALLOMER MA210 produced by Showa Denko K. K.) was used instead of the high-density polyethylene.

COMPARATIVE EXAMPLE 3

Filaments (4) having a size of 300 denier were produced in the same way as in Example 7 except that the deodorant was not used.

COMPARATIVE EXAMPLE 4

Filaments (5) having a size of 300 denier were produced in the same way as in Example 9 except that the deodorant was not used.

EXAMPLE 10

Deodorizing tests

The filaments (1) to (5) obtained in Examples 7 to 9 and Comparative Examples 3 and 4 (10 g each) were subjected to the same deodorizing tests as in Example 1 except that the concentration of ammonia was changed to 5,000 ppm and the concentration of hydrogen sulfide was changed to 50 ppm. The results are shown in Table 6.

The results given in Table 6 show that fibers obtained from the deodorizing resin composition of this invention have the excellent ability to deodorize basic odors and hydrogen sulfide odors.

TABLE 6

| Filaments | | Ammonia deodorizing rate (%) | | | Hydrogen sulfide deodorizing rate (%) |
|---|---|---|---|---|---|
| | | 1 hour later | 5 hours later | 24 hours later | 24 hours later |
| Invention | (1) | 52 | 83 | 100 | 100 |
| | (2) | 34 | 54 | 100 | 100 |
| | (3) | 52 | 83 | 100 | 100 |
| Comparison | (4) | 1.9 | 2.8 | 4.5 | 8.8 |
| | (5) | 1.5 | 2.7 | 4.4 | 8.3 |

EXAMPLE 11

One hundred parts of polyvinyl chloride (NIPEON A-33 produced by Nippon Zeon Co., Ltd.), 3 parts of a Ba-Zn type heat stabilizer, 6 parts of azodicarbonamide as a blowing agent, 15 parts of titanium oxide, 80 parts of calcium carbonate, 65 parts of dioctyl phthalate and 5 parts of mineral spirit were mixed by a mixing and grinding machine to form a slurry. The ene-adduct II in an amount corresponding to 5% of the total solids content of the slurry was added and the entire materials were further mixed for 5 minutes to form a paste sol. The sol was coated on paper to a thickness of 200 micrometers by a bar coater, and then heated at 210° C. for 60 seconds by a hot air-circulating type oven to form a foamed sheet (1b).

EXAMPLE 12

A foamed sheet (2b) was produced in the same way as in Example 11 except that a vinyl acetate/vinyl chloride copolymer (NIPEON A-135J produced by Nippon Zeon Co., Ltd.) was used instead of the polyvinyl chloride.

EXAMPLE 13

A foamed sheet (3b) was produced in the same way as in Example 11 except that the ene-adduct III was used instead of the ene-adduct II.

EXAMPLE 14

A foamed sheet (4b) was produced in the same way as in Example 11 except that ene-adduct IV was used instead of the ene-adduct II.

EXAMPLE 15

A foamed sheet (5b) was produced in the same way as in Example 11 except that 3-methyl-$\Delta^4$-tetrahydrophthalic anhydride was used instead of the ene-adduct II.

COMPARATIVE EXAMPLE 5

A foamed sheet (6b) was produced in the same way as in Example 11 except that the ene-adduct II was not added.

EXAMPLE 16

The ene-adduct II was dissolved in toluene to prepare a 5% toluene solution. The foamed sheet (6b) obtained in Comparative Example 5 was impregnated in the solution and dried to obtain a foamed sheet (7b) having a deodorant pick-up of 5%.

EXAMPLE 17

Deodorizing tests

The foamed sheets (1b) to (7b) obtained in Examples 11 to 16 and Comparative Example 5 each in an amount of 10 g were subjected to the same ammonia and hydrogen sulfide deodorizing tests as in Example 3.

The results are shown in Table 7.

The results given in Table 7 show that the deodorizing foams obtained from the deodorizing thermoplastic resin compositions of the invention have an excellent ability to deodorize ammonia and hydrogen sulfide.

TABLE 7

| Foamed sheet | | Ammonia deodorizing rate (%) 5 hours later | Ammonia deodorizing rate (%) 24 hours later | Hydrogen sulfide deodorizing rate (%) 24 hours later |
|---|---|---|---|---|
| Invention | 1b | 45 | 100 | 88 |
| | 2b | 43 | 100 | 85 |
| | 3b | 39 | 98 | 92 |
| | 4b | 34 | 93 | 86 |
| | 5b | 47 | 100 | 85 |
| | 7b | 48 | 100 | 90 |
| Comparison | 6b | 22 | 30 | 38 |

EXAMPLE 18

One gram of each of the paste sols prepared in Example 11 and Comparative Example 5 was taken into a 150 ml ampoule, and the ampoule was sealed up. The sealed ampoule was immersed for 10 minutes in an oil bath at 220° C. to foam the paste sol. The ampoule was opened, and the smell of the gaseous phase was examined. A strong ammonia smell was given off from the gaseous phase of the ampoule containing the sample of Comparative Example 5, whereas the gaseous phase of the ampoule containing the sample of Example 1 was odorless. The smell of the foam in the ampoule was also examined. The foam of Example 11 was odorless, whereas the foam of Comparative Example 5 gave off an ammonia smell.

The above fact indicates that when a deodorizing foam is produced by mixing the deodorant of the invention with a foamable thermoplastic resin and then foaming the resin, the dissipation of an ammonia smell occurring as a result of decomposition of the blowing agent is markedly suppressed.

EXAMPLE 19

Foamed sheets (1a), (3a), (5a) and (6a) were produced by operating in the same way as in Examples 11, 13 and 15 and Comparative Example 5 respectively except that the heat-treating time was changed to 30 seconds. Similarly, foamed sheets (1c), (3c), (5c) and (6c) were produced by changing the heating time to 90 seconds. The expansion ratios of these foamed sheets and the foamed sheets (1b), (3b), (5b) and (6b) were measured. The results are shown in Table 8.

TABLE 8

| | sheet number | Expansion ratio sheet mark a | b | c |
|---|---|---|---|---|
| Invention | 1 | 1.55 | 6.49 | 8.11 |
| | 3 | 1.50 | 6.46 | 8.03 |
| | 5 | 1.51 | 6.51 | 8.07 |
| Comparison | 6 | 1.50 | 6.49 | 8.10 |

The above results show that the deodorants used in the deodorizing foam of this invention do not affect the shape of the foams.

We claim:

1. A method for deodorizing malodorous components which comprises exposing the malodorous components or the atmosphere in which said malodorous components are present to a deodorant effective amount of an adduct of an alpha,beta-unsaturated dicarboxylic acid anhydride and an olefin or a derivative of said adduct as a deodorant active ingredient, said adduct being a Diels-Alder reaction product of an alpha,beta-unsaturated dicarboxylic acid anhydride and a diolefin hydrocarbon or an ene reaction product of an alpha,beta-unsaturated dicarboxylic acid anhydride and an olefinic hydrocarbon.

2. The method of claim 1 wherein said malodorous components comprise basic malodorous components.

3. The method of claim 2 wherein said basic malodorous components comprise ammonia or an amine compound.

4. The method of claim 1 wherein the malodorous components comprise hydrogen sulfide.

* * * * *